United States Patent
Zucker

(10) Patent No.: US 11,806,095 B2
(45) Date of Patent: Nov. 7, 2023

(54) TORQUE SENSOR WITH DECISION SUPPORT AND RELATED SYSTEMS AND METHODS

(71) Applicant: MAZOR ROBOTICS LTD., Caesarea (IL)

(72) Inventor: Ido Zucker, Tel Aviv (IL)

(73) Assignee: MAZOR ROBOTICS LTD., Caesarea (IL)

(*) Notice: Subject to any disclaimer, the term of this patent is extended or adjusted under 35 U.S.C. 154(b) by 454 days.

(21) Appl. No.: 16/903,596

(22) Filed: Jun. 17, 2020

(65) Prior Publication Data
US 2021/0393337 A1     Dec. 23, 2021

(51) Int. Cl.
| | |
|---|---|
| A61B 34/10 | (2016.01) |
| A61B 17/88 | (2006.01) |
| A61B 34/00 | (2016.01) |
| G01L 5/26 | (2006.01) |
| A61B 17/16 | (2006.01) |
| A61B 17/86 | (2006.01) |
| A61B 90/00 | (2016.01) |
| A61B 17/00 | (2006.01) |

(52) U.S. Cl.
CPC .......... *A61B 34/25* (2016.02); *A61B 17/1655* (2013.01); *A61B 17/86* (2013.01); *A61B 17/8875* (2013.01); *A61B 34/10* (2016.02); *G01L 5/26* (2013.01); *A61B 2017/00123* (2013.01); *A61B 2034/256* (2016.02); *A61B 2090/066* (2016.02)

(58) Field of Classification Search
CPC ............ A61B 17/8875–17/8894; A61B 34/10
See application file for complete search history.

(56) References Cited

U.S. PATENT DOCUMENTS

| | | | |
|---|---|---|---|
| 3,968,473 A | 7/1976 | Patton et al. | |
| 4,006,608 A * | 2/1977 | Vuceta | B25B 23/141 464/36 |
| 5,734,113 A | 3/1998 | Vogt et al. | |

(Continued)

FOREIGN PATENT DOCUMENTS

| | | |
|---|---|---|
| CA | 2408333 | 3/2001 |
| CN | 110200694 | 9/2019 |

(Continued)

OTHER PUBLICATIONS

Hu et al. "State Recognition of Pedicle Drilling With Force Sensing in a Robotic Spinal Surgical System," IEEE/ASME Transactions on Mechatronics, Feb. 2014, vol. 19, No. 1, pp. 357-365.

(Continued)

*Primary Examiner* — Zade Coley
(74) *Attorney, Agent, or Firm* — Sheridan Ross P.C.

(57) ABSTRACT

A surgical system includes a power tool that generates torque; a torque sensor for measuring a torque characteristic of the power tool; a user interface; at least one processor; and a memory. The memory stores instructions for execution by the at least one processor that, when executed, cause the at least one processor to: receive torque data from the torque sensor, the torque data corresponding to the measured torque characteristic; evaluate the torque data; and execute a predetermined action based on the evaluation.

20 Claims, 5 Drawing Sheets

(56) References Cited

U.S. PATENT DOCUMENTS

| | | | |
|---|---|---|---|
| 5,810,828 A | 9/1998 | Lightman et al. | |
| 6,132,435 A | 10/2000 | Young | |
| 6,978,846 B2* | 12/2005 | Kawai | B25B 23/1405 173/183 |
| 8,048,115 B2 | 11/2011 | Winslow et al. | |
| 8,092,457 B2 | 1/2012 | Oettinger et al. | |
| 8,821,493 B2 | 9/2014 | Anderson | |
| 8,894,654 B2 | 11/2014 | Anderson | |
| 9,204,885 B2 | 12/2015 | McGinley | |
| 9,265,551 B2 | 2/2016 | Kust et al. | |
| 9,283,048 B2 | 3/2016 | Kostrzewski et al. | |
| 2005/0045353 A1* | 3/2005 | Kawai | B25B 21/02 173/183 |
| 2006/0243464 A1 | 11/2006 | Heinz | |
| 2007/0119063 A1 | 5/2007 | Kim | |
| 2012/0310247 A1 | 12/2012 | Hsieh | |
| 2014/0165796 A1 | 6/2014 | Gauthier et al. | |
| 2014/0260837 A1 | 9/2014 | Gauthier et al. | |
| 2015/0351819 A1* | 12/2015 | Gustafson | A61B 17/8875 606/104 |
| 2015/0366624 A1 | 12/2015 | Kostrzewski et al. | |
| 2016/0151120 A1 | 6/2016 | Kostrzewski et al. | |
| 2016/0354162 A1 | 12/2016 | Yen et al. | |
| 2017/0151025 A1 | 6/2017 | Mewes et al. | |
| 2017/0348037 A1* | 12/2017 | Sexson | A61B 17/1617 |
| 2018/0110573 A1 | 4/2018 | Kostrzewski | |
| 2018/0289432 A1 | 10/2018 | Kostrzewski et al. | |
| 2018/0325608 A1 | 11/2018 | Kang et al. | |
| 2019/0029697 A1 | 1/2019 | Anderson et al. | |
| 2019/0269469 A1 | 9/2019 | Busch, Jr. et al. | |
| 2021/0347020 A1* | 11/2021 | Friberg | B25B 21/02 |

FOREIGN PATENT DOCUMENTS

| | | |
|---|---|---|
| EP | 0912140 | 8/2004 |
| KR | 10-2007430 | 10/2019 |
| WO | WO 2007/056255 | 5/2007 |
| WO | WO 2013/050851 | 4/2013 |
| WO | WO 2017/214194 | 12/2017 |

OTHER PUBLICATIONS

Jin et al. "Design and control strategy of robotic spinal surgical system," The 2011 IEEE/ICME International Conference on Complex Medical Engineering, May 22-25, 2011 (abstract only).

Lee et al. "An Implementation of Sensor-Based Force Feedback in a Compact Laparoscopic Surgery Robot," ASAIO Journal, Jan. 2009, vol. 55, No. 1, pp. 83-85.

Tian et al. "A Robot-Assisted Surgical System Using a Force-Image Control Method for Pedicle Screw Insertion," PLOS ONE, Jan. 2014, vol. 9, No. 1, article e86346, 10 pages.

Wang et al. "Force-based control of a compact spinal milling robot," The International Journal of Medical Robotics and Computer Assisted Surgery, Jun. 2010, vol. 6, No. 2, pp. 178-185 (abstract only).

International Search Report and Written Opinion for International (PCT) Patent Application No. PCT/US2021/033850, dated Sep. 2, 2021, 11 pages.

* cited by examiner

TORQUE SENSOR WITH DECISION SUPPORT AND RELATED SYSTEMS AND METHODS

FIELD

The present technology generally relates to robot-assisted surgery, and more particularly relates to the use of power tools during robot-assisted surgery.

BACKGROUND

Various surgical procedures involve the use of one or more tools for transmitting torque, whether for drilling, tapping, inserting a screw, or otherwise. Surgical robots are useful for holding and/or operating one or more tools or devices during a surgery, and may operate autonomously (e.g., without any human input during operation), semi-autonomously (e.g., with some human input during operation), or non-autonomously (e.g., only as directed by human input).

SUMMARY

A surgical system according to one embodiment of the present disclosure comprises: a power tool that generates torque; a torque sensor for measuring a torque characteristic of the power tool; a user interface; at least one processor; and a memory. The memory stores instructions for execution by the at least one processor that, when executed, cause the at least one processor to: receive torque data from the torque sensor, the torque data corresponding to the measured torque characteristic; evaluate the torque data; and execute a predetermined action based on the evaluation.

The measured torque characteristic may be a peak torque, and the evaluation may comprise comparing the peak torque to a predetermined threshold. When the peak torque exceeds the predetermined threshold, the predetermined action may comprise stopping the power tool. The measured torque characteristic may be an accumulated torque, and the evaluation may comprise comparing the accumulated torque to a predetermined threshold. When the accumulated torque is less than the predetermined threshold, the predetermined action may comprise causing a recommendation to be displayed via a user interface. The power tool may be a screwdriver, and the recommendation may comprise a recommendation to select a larger screw.

The power tool may be a screwdriver, the torque data may correspond to the measured torque characteristic during insertion with the screwdriver of a first screw, and the memory may store additional instructions for execution by the at least one processor that, when executed, further cause the at least one processor to receive second torque data from the torque sensor, the second torque data corresponding to the measured torque characteristic during insertion with the screwdriver of a second screw. The evaluating may comprise evaluating the torque data and the second torque data.

The predetermined action may comprise stopping the power tool and requesting user input. The predetermined action may comprise modifying a surgical plan based on the evaluation.

A surgical method according to at least another embodiment of the present disclosure comprises: operating a power screwdriver to insert a plurality of screws into an anatomical feature of a patient; measuring, with a torque sensor operatively connected to the power screwdriver, a torque characteristic of the power screwdriver during insertion of each of the plurality of screws to yield torque data; and modifying a preoperative plan for insertion of the plurality of screws based on the torque data.

Modifying the preoperative plan may comprise removing from the preoperative plan at least one screw that was to be inserted into the anatomical feature of the patient. Modifying the preoperative plan may comprise adding to the preoperative plan at least one additional screw to be inserted into the anatomical feature of the patient. Modifying the preoperative plan may comprise changing a characteristic of at least one screw identified in the preoperative plan for insertion into the anatomical feature of the patient. The torque characteristic may comprise peak torque, accumulated torque, or RMS torque.

A device according to another embodiment of the present disclosure comprises: a torque sensor for measuring a torque characteristic during a drilling, tapping, or screw insertion surgical procedure; a processor; and a memory. The memory stores instructions for execution by the processor that, when executed, cause the processor to: receive data from the torque sensor corresponding to the measured torque characteristic; cause the drilling, tapping, or screw insertion surgical procedure to stop when the measured torque characteristic satisfies a predetermined criterion; generate a recommendation based on at least one of the measured torque characteristic or the predetermined criterion; and cause the recommendation to be displayed via a user interface.

The recommendation may correspond to changing one of a tap size, a drilling diameter, or a screw size. The recommendation may correspond to adding or removing a screw from a preoperative plan. The predetermined criterion may be based on historical data corresponding to measured torque characteristics and patient outcomes. The memory may store additional instruction for execution by the processor that, when executed, cause the processor to: receive a user input in response to the recommendation; and cause the drilling, tapping, or screw insertion surgical procedure to proceed based on the user input.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
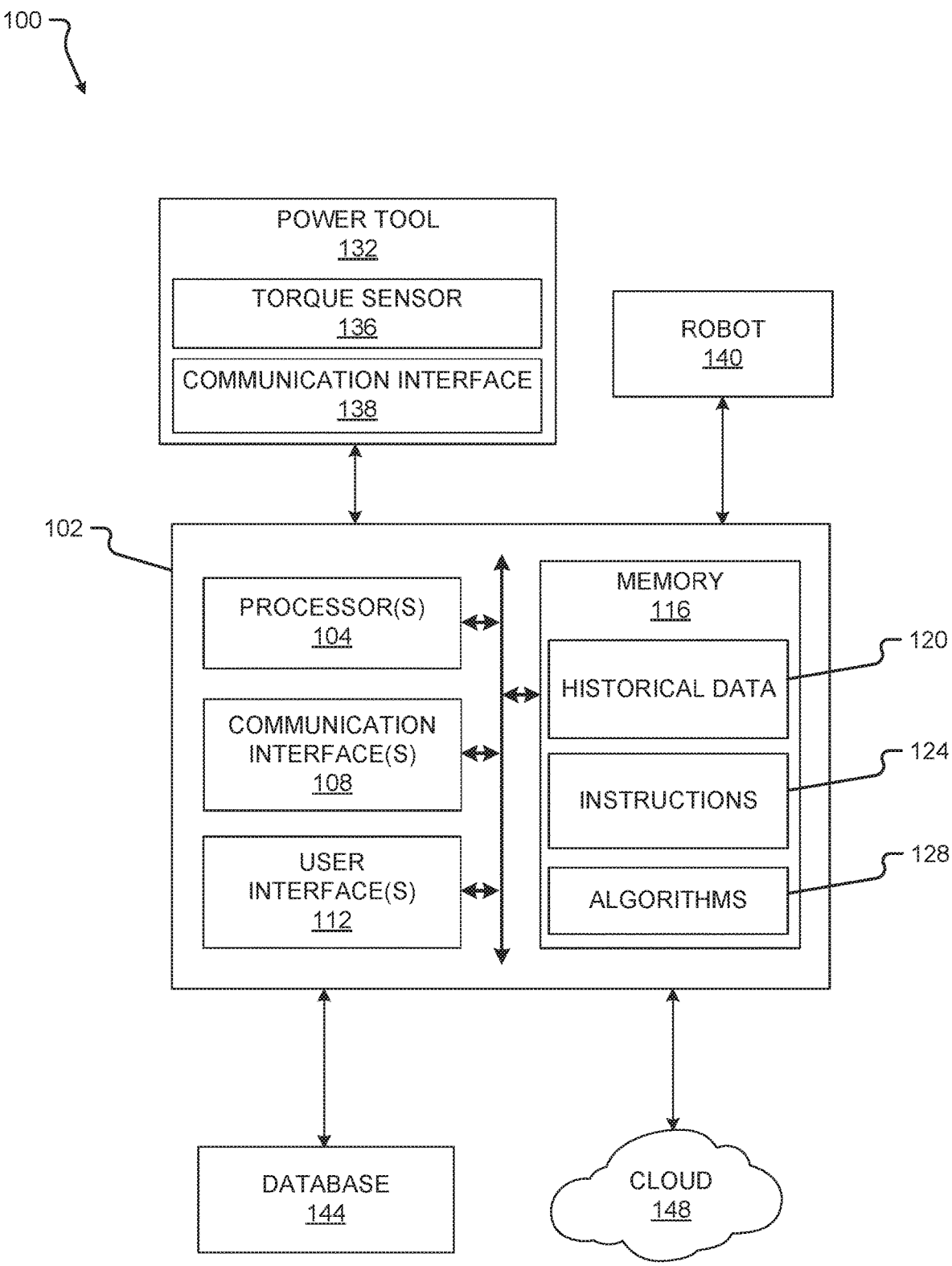
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

A surgeon carrying out a drilling, tapping, and/or screw insertion procedure manually receives tactile feedback throughout the procedure and is thus able to sense whether the procedure is normal or abnormal. For example, a surgeon inserting a screw manually (e.g., with a manual screwdriver) may sense that the screw is advancing more easily than normal, or alternatively, is more difficult to advance than normal. Based on this sensed feedback, the surgeon may make an intraoperative decision to deviate from a preoperative plan—whether by selecting a larger or a smaller screw, or by re-drilling or re-tapping the bone (e.g., with a different-sized drill bit or tap), or by opting to skip a screw, or insert an additional screw, or otherwise.

When power tools are used for the drilling, tapping, and/or screw insertion procedure, the amount of tactile feedback received by the surgeon decreases. If the surgeon is holding the power tool, the surgeon may or may not receive enough tactile feedback to determine whether a change in a predetermined plan is necessary. However, particularly when a power tool is operated autonomously—e.g., both held and operated by a robot—the information previously gained by the surgeon through tactile feedback is unavailable, such that appropriate deviations from a preoperative or other surgical plan are less likely to be identified or made, with a potentially negative effect on surgical outcomes.

The present disclosure describes the use of a torque sensor and a decision support system to monitor the quality of a given procedure and enable appropriate adjustments to a surgical procedure and/or to a preoperative or other surgical plan to be made, even in the absence of a surgeon or other human user receiving tactile feedback. The present disclosure thus beneficially enables needed or otherwise appropriate deviations from a preoperative or other surgical plan to be identified and made, thus helping to ensure that surgical outcomes are not negatively affected by removal of a surgeon from the direct carrying out of the procedure. In some embodiments of the present disclosure, a surgeon or other operator may monitor or otherwise be indirectly involved in a procedure being carried out by a surgical robot and provide input as necessary, while in other embodiments, a surgical robot may carry out a procedure completely autonomously.

Embodiments of the present disclosure are configured to provide information to a surgeon regarding the quality of a given procedure (e.g., a drilling, tapping, and/or screw insertion procedure), and in some embodiments to provide a recommendation to the surgeon as well (e.g., increase or decrease the size of a drill, tap, or screw; skip some or all of the drilling, tapping, and/or screw insertion procedure in question; add or remove one or more elements from a preoperative or other surgical plan). Based on input received from the surgeon or other operator in response to the information and/or recommendation, the procedure may continue (albeit with one or more changes indicated by the input).

Where a surgical robot is utilized to carry out a given procedure autonomously (e.g., with no human intervention), information detected by a torque sensor may be used to evaluate the quality of a given procedure, and one or more decision-making criteria may be applied to determine whether to change a preoperative or other surgical plan (e.g., to increase or decrease the size of a drill, tap, or screw, or otherwise modify the procedure in question; to skip some or all of the drilling, tapping, and/or screw insertion procedure in question; to add or remove one or more elements from a preoperative or other surgical plan) based on the evaluation.

Embodiments of the present disclosure may utilize machine learning to identify, from historical data regarding a plurality of drilling, tapping, and/or screw insertion procedures, torque data collected therefrom, and associated patient outcomes (which may be measured or otherwise evaluated immediately, one year, five years, ten years, twenty years, and/or at any other interval following the procedures in question), one or more criteria, thresholds, and/or other parameters for use in connection with the present disclosure to improve chances of a positive outcome.

The present disclosure solves several technical problems, including but not limited to (1) that the use of a power tool for drilling, tapping, and/or screw insertion procedures, while beneficial in terms of reducing the workload of a surgeon, deprives the surgeon of tactile feedback regarding the quality of the procedures, which could lead to potentially harmful or negative consequences for the patient; (2) that a surgical robot carrying out a drilling, tapping, and/or screw insertion procedure autonomously cannot rely on a surgeon to monitor or verify the quality of the procedure, particularly given that the surgeon has no way to receive tactile feedback regarding the quality of the procedure during the procedure; and (3) that a preoperative or other surgical plan may not reflect important information obtained during a drilling, tapping, and/or screw insertion procedure, and thus may need to be updated intraoperatively (and possibly autonomously) to ensure that the plan as ultimately executed accomplishes the intended purpose(s) thereof.

Turning now to FIG. 1, a block diagram of a system 100 according to at least one embodiment of the present disclosure is shown. The system 100 may be used, for example: to carry out a drilling, tapping, screw insertion, or other surgical task or procedure involving application of torque; to carry out one or more aspects of one or more of the methods disclosed herein; to improve patient outcomes in connection with a drilling, tapping, screw insertion, or other surgical task or procedure; or for any other useful purpose. The system 100 comprises a computing device 102, a power tool 132, a robot 142, a database 144, and a cloud 148. Notwithstanding the foregoing, systems according to other embodiments of the present disclosure may omit any one or more of the robot 140, database 144, and/or the cloud 148. Additionally, systems according to other embodiments of the present disclosure may arrange one or more components of the system 100 differently (e.g., the power tool 132 may comprise one or more of the components of the computing device 102, and/or vice versa).

The computing device 102 comprises at least one processor 104, at least one communication interface 108, at least one user interface 112, and at least one memory 116. A computing device according to other embodiments of the present disclosure may omit one or both of the communication interface(s) 108 and/or the user interface(s) 112.

The at least one processor 104 of the computing device 102 may be any processor identified or described herein or any similar processor. The at least one processor 104 may be configured to execute instructions 124 stored in the at least one memory 116, which instructions 124 may cause the at least one processor 104 to carry out one or more computing steps utilizing or based on data received, for example, from the power tool 132, the robot 140, the database 144, and/or the cloud 148, and/or stored in the memory 116 (e.g., historical data 120). The instructions 124 may also cause the at least one processor 104 to utilize one or more algorithms 128 stored in the memory 116. In some embodiments, the at least one processor 104 may be used to control the power tool 132 and/or the robot 140 during a surgical procedure, including during a drilling, tapping, screw insertion, or other procedure being carried out autonomously or semi-autonomously by the robot 140 using the power tool 132.

The computing device 102 may also comprise at least one communication interface 108. The at least one communication interface 108 may be used for receiving torque data, a surgical plan or other planning data, or other information from an external source (such as the power tool 132, the robot 140, the database 144, the cloud 148, and/or a portable storage medium (e.g., a USB drive, a DVD, a CD)), and/or for transmitting instructions, images, or other information from the at least one processor 104 and/or the computing device 102 more generally to an external system or device (e.g., another computing device 102, the power tool 132, the robot 140, the database 144, the cloud 148, and/or a portable storage medium (e.g., a USB drive, a DVD, a CD)). The at least one communication interface 108 may comprise one or more wired interfaces (e.g., a USB port, an ethernet port, a Firewire port) and/or one or more wireless interfaces (configured, for example, to transmit information via one or more wireless communication protocols such as 802.11a/b/g/n, Bluetooth, Bluetooth low energy, NFC, ZigBee, and so forth). In some embodiments, the at least one communication interface 108 may be useful for enabling the device 102 to communicate with one or more other processors 104 or computing devices 102, whether to reduce the time needed to accomplish a computing-intensive task or for any other reason.

The at least one user interface 112 may be or comprise a keyboard, mouse, trackball, monitor, television, touchscreen, button, joystick, switch, lever, and/or any other device for receiving information from a user and/or for providing information to a user of the computing device 102. The at least one user interface 112 may be used, for example, to receive a user selection or other user input in connection with any step of any method described herein; to receive a user selection or other user input regarding one or more configurable settings of the computing device 102, the power tool 132, the robot 140, and/or of another component of the system 100; to receive a user selection or other user input regarding how and/or where to store and/or transfer data received, modified, and/or generated by the computing device 102; and/or to display information (e.g., text, images) and/or play a sound to a user based on data received, modified, and/or generated by the computing device 102. Notwithstanding the inclusion of the at least one user interface 112 in the system 100, the system 100 may automatically (e.g., without any input via the at least one user interface 112 or otherwise) carry out one or more, or all, of the steps of any method described herein.

Although the at least one user interface 112 is shown as part of the computing device 102, in some embodiments, the computing device 102 may utilize a user interface 112 that is housed separately from one or more remaining components of the computing device 102. In some embodiments, the user interface 112 may be located proximate one or more other components of the computing device 102, while in other embodiments, the user interface 112 may be located remotely from one or more other components of the computer device 102.

The at least one memory 116 may be or comprise RAM, DRAM, SDRAM, other solid-state memory, any memory described herein, or any other tangible non-transitory memory for storing computer-readable data and/or instructions. The at least one memory 116 may store information or data useful for completing, for example, any step of the methods 300, 350, 400, or 500 described herein. The at least one memory 116 may store, for example, historical data 120, instructions 124, and/or algorithms 128. In some embodiments, the memory 116 may also store one or more preoperative and/or other surgical plans; one or more images of one or more patients, including in particular of an anatomical feature of the one or more patients on which one or more surgical procedures is/are to be performed; torque data received from the power tool 132 or elsewhere; and/or other information useful in connection with the present disclosure.

The historical data 120 may comprise data about a plurality of surgical procedures previously carried out and involving one or more of a drilling, tapping, and/or screw insertion procedure. The historical data 120 may comprise information about each such procedure (e.g., date and time of the procedure, anatomical location of the procedure, type of procedure, original surgical plan for the procedure, actual (e.g., as-executed) surgical plan for the procedure); information about the patient on whom the procedure was performed (e.g., patient age, gender, height, weight, relevant health information, position during procedure); torque data gathered during the procedure (e.g., peak torque, accumulated torque, RMS torque); and/or outcome data (e.g., screw status over time, including whether each screw inserted during the procedure remained secure, loosened, and/or had to be replaced; status of the bone in which the screw(s) was/were placed, including whether the bone cracked or fractured over time; levels of pain (if any) experienced by the patient over time). In some embodiments, the historical data 120 may be used by a machine learning engine to identify correlations between or among, on the one hand, one or more of peak torque during a procedure, accumulated torque during a procedure, RMS torque during a procedure, and/or any other torque characteristic during a procedure, and on the other hand, one or more procedure outcomes, so as to yield one or more thresholds, criteria, or algorithms, and/or other parameters that can be utilized during a surgical procedure to increase the likelihood of a positive procedural outcome.

The instructions 124, as described above, may be or comprise any instructions for execution by the at least one processor 104 that cause the at least one processor to carry out one or more steps of any of the methods described herein. The instructions 124 may be or comprise instructions for carrying out a drilling, tapping, and/or screw insertion procedure. The instructions 124 may additionally or alternatively enable the at least one processor 104, and/or the computing device 102 more generally, to operate as a machine learning engine that receives historical data 120 and outputs one or more thresholds, criteria, algorithms, and/or other parameters that can be utilized during a drilling, tapping, and/or screw insertion procedure, and/or during any other surgical procedure in which torque measurements may be relevant, to increase the likelihood of a positive procedural outcome.

The algorithms 128 may be or comprise any algorithms useful for converting torque data received from a torque sensor 136 into meaningful torque information. The algorithms 128 may also be or comprise any algorithms useful for applying one or more thresholds, criteria, and/or other parameters to torque data (including any information derived therefrom) to evaluate the torque data. The algorithms 128 may further be or comprise any algorithms useful for generating one or more recommendations to a surgeon or other user of the system 100 based on torque data received from a torque sensor 136 and/or an evaluation of such torque data, and/or for modifying a preoperative or other surgical plan based on torque data received from a torque sensor 136 and/or an evaluation of such torque data. The algorithms 128 may further be or comprise algorithms useful for controlling the power tool 132 and/or the robot 140.

The power tool 132 may be a power drill, power screwdriver, or any other device that generates torque for the purpose of accomplishing mechanical work on an anatomical feature of a patient. The power tool 132 may comprise a dedicated processor for executing instructions stored in a dedicated memory of the power tool 132, or the power tool 132 may be controlled in whole or in part by the at least one processor 104 of the computing device 102, or the power tool 132 may be configured to operate without any processor control. For example, the power tool 132 may comprise a switch, trigger, or other mechanism that can be moved between a plurality of positions to control operation of the power tool 132.

The power tool 132 comprises a torque sensor 136 and a communication interface 138. In some embodiments, the torque sensor 136 and the communication interface 138 may comprise a single device within or otherwise secured to the power tool 132. The torque sensor 136 may be configured to measure one or more torque characteristics during use of the power tool 132 for a given drilling, tapping, screw insertion, or other procedure, such as peak torque, accumulated torque, and/or root mean square, or "RMS," torque. Peak torque is the maximum amount of instantaneous torque generated during the course of the procedure. Accumulated torque is the total amount of torque generated during the course of the procedure (obtained, for example, by integrating instantaneous torque over time). RMS torque, or root mean square torque, is the square root of the mean of all of the squares of the instantaneous torques generated during the procedure.

The communication interface 138 may be the same as or similar to the communication interface 108. For example, the communication interface 138 may be utilized for receiving operating instructions and/or control signals from an external source (such as the computing device 102, the robot 140), and/or for transmitting torque data (e.g., corresponding to one or more torque characteristics measured by the torque sensor 136) or other information to an external system or device (e.g., the computing device 102, the robot 140, the database 144, the cloud 148, and/or a portable storage medium (e.g., a USB drive, a DVD, a CD)). The communication interface 138 may comprise one or more wired interfaces (e.g., a USB port, an ethernet port, a Firewire port) and/or one or more wireless interfaces (configured, for example, to transmit information via one or more wireless communication protocols such as 802.11a/b/g/n, Bluetooth, Bluetooth low energy, NFC, ZigBee, and so forth). In some embodiments, the communication interface 138 may be useful for enabling the device 102 to communicate with one or more other processors 104 or computing devices 102, whether to reduce the time needed to accomplish a computing-intensive task or for any other reason.

In some embodiments, the power tool 132 may comprise more than one power tool 132.

The robot 140 may be any surgical robot or surgical robotic system. The robot 140 may be or comprise, for example, the Mazor X™ Stealth Edition robotic guidance system. The robot 140 may comprise a base that supports a robotic arm configured to hold the power tool 132. The robot 140 may comprise one or more robotic arms, each of which may be configured to hold a power tool such as the power tool 132. The robot 140 may, in some embodiments, assist with a surgical procedure (e.g., by holding a tool in a desired trajectory or pose and/or supporting the weight of a tool while a surgeon or other user operates the tool, or otherwise) and/or automatically carry out a surgical procedure.

The database 144 may store any information that is shown in FIG. 1 as being stored in the memory 116, including historical data such as the historical data 120, instructions such as the instructions 124, and/or algorithms such as the algorithms 128. In some embodiments, the database 144 stores one or more preoperative or other surgical plans. The database 144 may additionally or alternatively store, for example, information about or corresponding to one or more characteristics of the power tool 132, available drill bits for use by the power tool 132, available taps and/or dies for use by the power tool 132, available screws for insertion by the power tool 132, and/or other information regarding available tools and/or equipment for use in connection with a surgical procedure. The database 144 may be configured to provide any such information to the computing device 102, the power tool 132, the robot 140, or to any other device of the system 100 or external to the system 100, whether directly or via the cloud 148. In some embodiments, the database 144 may be or comprise part of a hospital image storage system, such as a picture archiving and communication system (PACS), a health information system (HIS), and/or another system for collecting, storing, managing, and/or transmitting electronic medical records including image data. Also in some embodiments, the memory 116 may store any of the information described above.

The cloud 148 may be or represent the Internet or any other wide area network. The computing device 102 may be connected to the cloud 148 via the communication interface 108, using a wired connection, a wireless connection, or both. In some embodiments, the computing device 102 may communicate with the database 144 and/or an external device (e.g., a computing device) via the cloud 148.

Figure 2:
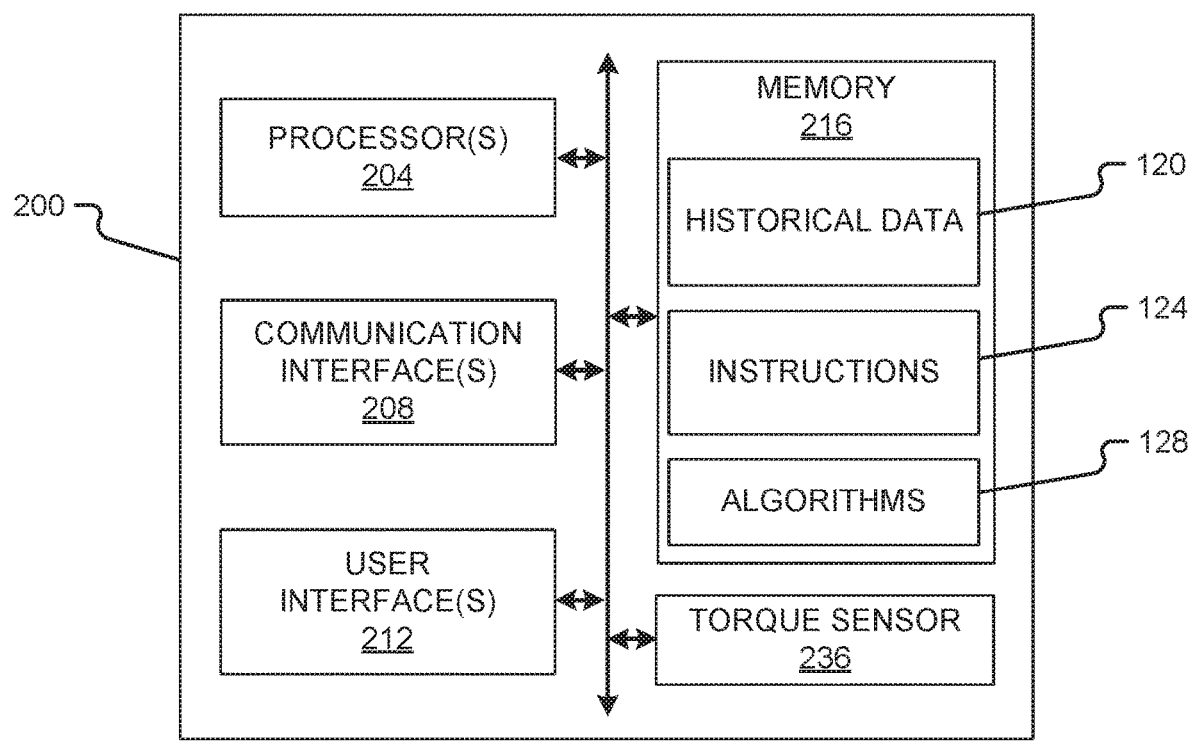
FIG. 2 is a block diagram of a device according to at least one embodiment of the present disclosure.

With reference now to FIG. 2, a power tool 200 may be a power drill, power screwdriver, or any other device that generates torque for the purpose of accomplishing mechanical work on an anatomical feature of a patient. The power tool 200 comprises one or more processors 204, one or more communication interfaces 208, one or more user interfaces 212, at least one memory 216, and at least one torque sensor 236. Notwithstanding the layout of the power tool 200 as illustrated in FIG. 2, power tools according to other embodiments of the present disclosure may comprise more or fewer components than the power tool 200.

The one or more processors 204 may be the same as or similar to the at least one processor 104. For example, the one or more processor 204 of the power tool 200 may be any processor(s) identified or described herein or any similar processor(s). The one or more processors 204 may be configured to execute instructions 124 stored in the at least one memory 216, which instructions 124 may cause the one or more processors 204 to carry out one or more computing steps utilizing or based on data received, for example, from the torque sensor 236 or an external device such as a robot 140, a database 144, and/or a cloud 148, and/or stored in the memory 116 (e.g., historical data 120). The instructions 124 may also cause the one or more processors 204 to utilize one or more algorithms 128 stored in the memory 116. In some embodiments, the one or more processors 204 may be used to control the power tool 200 during a surgical procedure, including during a drilling, tapping, screw insertion, or other procedure being carried out autonomously or semi-autonomously using the power tool 132.

The at least one communication interface 208 may be the same as or similar to the at least one communication interface 108. For example, the at least one communication interface 208 may be used for receiving a surgical plan or other planning data, or other information from an external source (such as a computing device 102, a robot 140, a database 144, a cloud 148, and/or a portable storage medium (e.g., a USB drive, a DVD, a CD)), and/or for transmitting torque data (e.g., corresponding to a torque characteristic measured by the torque sensor 236) or other information from the at least one processor 204 and/or the power tool 200 more generally to an external system or device (e.g., a computing device 102, a power tool 132, a robot 140, a database 144, a cloud 148, and/or a portable storage medium (e.g., a USB drive, a DVD, a CD)). The at least one communication interface 208 may comprise one or more wired interfaces (e.g., a USB port, an ethernet port, a Firewire port) and/or one or more wireless interfaces (configured, for example, to transmit information via one or more wireless communication protocols such as 802.11a/b/g/n, Bluetooth, Bluetooth low energy, NFC, ZigBee, and so forth). In some embodiments, the at least one communication interface 208 may be useful for enabling the power tool 200 to communicate with one or more other processors, whether to reduce the time needed to accomplish a computing-intensive task or for any other reason.

The at least one user interface 212 may be the same as or similar to the at least one user interface 112. For example, the at least one user interface 212 may be or comprise a keyboard, mouse, trackball, monitor, television, touchscreen, button, joystick, switch, lever, trigger, and/or any other device for receiving input and/or information from a user and/or for providing information to a user of the power tool 200. The at least one user interface 212 may be used, for example, to receive a user selection or other user input in connection with any step of any method described herein; to receive a user selection or other user input regarding one or more configurable settings of the power tool 200; to receive a user selection or other user input regarding how and/or where to store and/or transfer data received, modified, and/or generated by the power tool 200 (including the torque sensor 236 and/or any other component of the power tool 200); and/or to display information (e.g., text, images) and/or to play a sound to a user based on data received, modified, and/or generated by the power tool 200. Notwithstanding the inclusion of the at least one user interface 212 in the power tool 200, the tool 200 may be configurable to operate automatically (e.g., under the control of the one or more processors 204, without any input via the at least one user interface 212 or otherwise) to carry out one or more, or all, of the steps of any method described herein.

Although the at least one user interface 212 is shown as part of the power tool 200, in some embodiments, the power tool 200 may utilize a user interface 212 that is housed separately from one or more remaining components of the power tool 200. In some embodiments, the user interface 212 may be located proximate one or more other components of the power tool 200, while in other embodiments, the user interface 212 may be located remotely from one or more other components of the power tool 200.

The at least one memory 216 may be the same as or similar to the memory 116. For example, the at least one memory 216 may be or comprise RAM, DRAM, SDRAM, other solid-state memory, any memory described herein, or any other tangible non-transitory memory for storing computer-readable data and/or instructions. The at least one memory 216 may store information or data useful for completing, for example, any step of the methods 300, 350, 400, or 500 described herein. The at least one memory 216 may store, for example, historical data 120, instructions 124, and/or algorithms 128, each of which is described in greater detail above. In some embodiments, the at least one memory 116 may also store one or more preoperative and/or other surgical plans; one or more images of one or more patients, including in particular of an anatomical feature of the one or more patients on which one or more surgical procedures is/are to be performed; torque data received from at least one torque sensor 236; and/or other information useful in connection with the present disclosure.

The torque sensor 236 may be the same as or similar to the torque sensor 136. For example, the torque sensor 236 may be configured to measure one or more torque characteristics during use of the power tool 200 for a given drilling, tapping, screw insertion, or other procedure, such as peak torque, accumulated torque, and/or RMS torque.

Figure 3A:
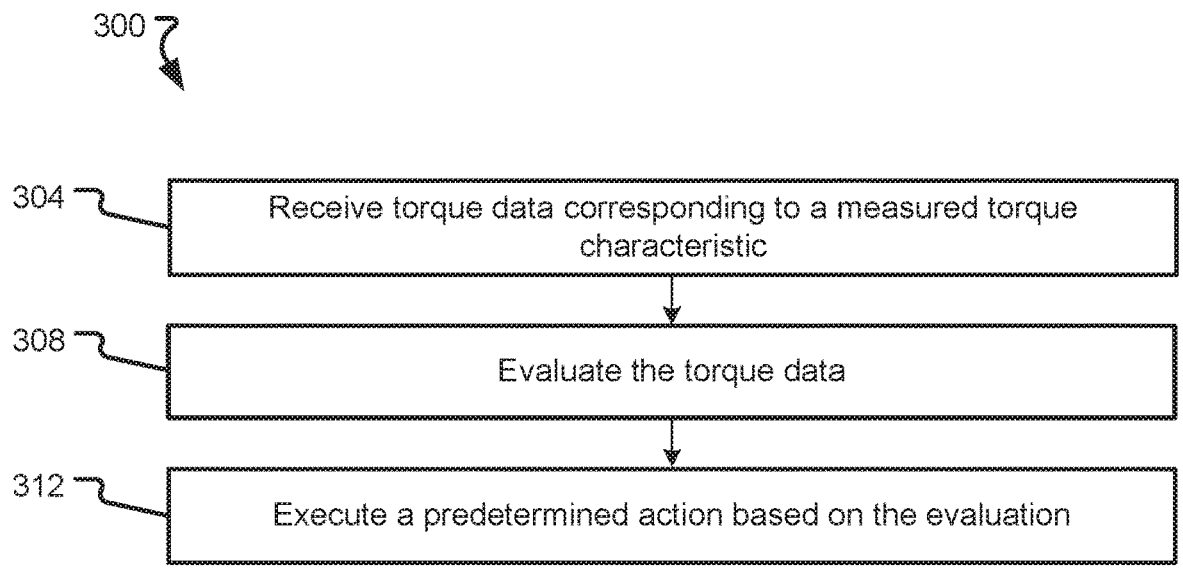
FIG. 3A is a flowchart of a method according to at least one embodiment of the present disclosure.

Turning now to FIG. 3A, a method 300 of using a system such as the system 100, or a device such as the device 200, during a surgical procedure comprises receiving torque data corresponding to a measured torque characteristic (step 304). The torque data may be raw data output by a torque sensor 136 or 236, or the torque data may be processed data generated based on raw data output by the torque sensor 136 or 236. The measured torque characteristic may be or correspond to one or more of peak torque, accumulated torque, RMS torque, and/or any other torque characteristic. A measured torque characteristic, as used herein, includes any torque characteristic actually measured by a torque sensor such as the torque sensors 136 and/or 236, and any torque characteristic calculated based on actual measurements by a torque sensor such as the torque sensors 136 and/or 236. The torque data may be received directly from the torque sensor 136 or 236, or via one or more processors, communication interfaces, or other components described herein. For example, the torque data may be transmitted from a communication interface 138 to a cloud 148, and from the cloud 148 to the communication interface 112 before arriving at the processor 104. On the other hand, where the power tool 200 is being used, for example, the torque data may simply be transmitted across an internal bus from the torque sensor 236 to the processor 204, whether directly or via the communication interface 208 and/or the memory 216.

The method 300 also comprises evaluating the torque data (step 308). The evaluating may comprise comparing the torque data to a predetermined threshold (e.g., a predetermined threshold stored in the at least one memory 116 or 216). For example, where the torque data corresponds to peak torque, the peak torque may be compared to a maximum peak torque threshold that represents, e.g., a maximum desirable peak torque or a maximum safe peak torque. Where the torque data corresponds to accumulated torque and/or RMS torque, a similar comparison may be made to a predetermined maximum threshold for accumulated torque and/or RMS torque, respectively.

The evaluating may also comprise applying one or more predetermined criteria to the torque data, or otherwise analyzing or considering the torque data using one or more predetermined criteria. The predetermined criteria may be based on or otherwise configured to evaluate more than a single measured torque characteristic. For example, the predetermined criteria may be based on or otherwise configured to evaluate two or more of peak torque, accumulated torque, and/or RMS torque for a given drilling, tapping, and/or screw insertion procedure. The predetermined criteria may additionally or alternatively be based on or otherwise configured to evaluate one or more measured torque characteristics for a plurality of drilling, tapping, and/or screw insertion procedures for a single patient, and/or on a single surgical plan. In some embodiments, the predetermined criteria may additionally or alternatively be based on or otherwise configured to evaluate a surgical plan in light of one or more measured torque characteristics.

In some embodiments, the predetermined criteria may be based on historical data such as the historical data 120. For example, where historical data regarding one or more measured torque characteristics during a plurality of surgical procedures (e.g., drilling, tapping, screw insertion, or other surgical procedures) is available, and particularly where such historical data comprises information about patient outcomes, then the historical data may be used to generate one or more predetermined criteria useful for evaluating, for example, a likely outcome of the current procedure based on available torque data; whether a likely outcome of the current procedure may be improved by adjusting one or more aspects of a surgical plan for the current procedure; and/or whether a likely outcome of the surgical procedure may be improved by modifying one or more aspects of the procedure, whether or not the surgical plan is modified (e.g., in a manner that will affect one or more measured torque characteristics of the procedure going forward). Thus, for example, if the historical data suggests that outcomes are poor when peak torque reaches or surpasses a specific threshold during insertion of a screw, the predetermined criteria may comprise evaluating whether peak torque for the current procedure is approaching the specific threshold in question, and if so, removing the screw being inserted and inserting instead a smaller screw or a screw that otherwise requires less torque to insert.

The evaluating may further comprise applying any other standard or parameter to the torque data.

Also, the evaluation may happen once, periodically, or continuously. Where the torque data is received once, the evaluating may also occur only once. Where the torque data is received periodically, the evaluating may also occur periodically. Where the torque data is received continuously (e.g., via live stream), the evaluating may likewise occur continuously (e.g., in real time or near real time).

The method 300 also comprises executing a predetermined action based on the evaluation (step 312). The predetermined action may simply be, or may include, stopping the power tool corresponding to the measured torque characteristic. For example, if the evaluating determines that the peak torque has reached or exceeded a predetermined threshold, then the power tool may be stopped to prevent potential harm to the patient (including to the patient's anatomy). Once stopped, the power tool may, in some embodiments, be returned to operation only based on user input, for example so as to allow a surgeon or other attendant to review the torque data and/or the results of the evaluation. The user input may be, for example, an acknowledgment of a warning that the peak torque (or other measured torque characteristic of concern) has reached or exceeded a threshold value or has otherwise approached a predetermined limit.

The predetermined action may be or include generating a recommendation as to how to proceed in light of the evaluation, and/or causing such a recommendation to be displayed to a user via a user interface such as the user interface 112 or 212. For example, if the evaluating determines that one or more of the peak torque, the accumulated torque, and/or the RMS torque exceeds a respective predetermined threshold and/or falls within a certain respective range, then the predetermined action may be or include generating a recommendation to use a fresh drill bit and/or to use a larger or smaller drill bit; to use a fresh tap or die and/or to use a larger or smaller tap or die; to use a larger or smaller screw; to change a setting of the power tool; and/or to modify a surgical plan (whether by adding one or more steps and/or screws, modifying details regarding one or more steps and/or screws, or by removing one or more steps and/or screws, or any combination of the foregoing). Unless specified otherwise, references to "larger" or "smaller" drill bits, taps, dies, and/or screws herein refer to drill bits, taps, dies, and/or screws that require more or less torque, respectively, to use or insert.

Particularly in embodiments where a surgical robot is operating the power tool autonomously, any action that might be recommended to a surgeon in other embodiments might be automatically carried out by the surgical robot. Thus, the predetermined action may be or comprise, for example, changing to a fresh drill bit of the same size or switching to a larger or smaller drill bit; changing to a fresh tap or die and/or switching to a larger or smaller tap or die; replacing a current screw with a larger or smaller (whether in terms of torque, length, diameter, or otherwise) screw; changing a setting of the power tool; and/or modifying a surgical plan (whether by adding one or more steps and/or screws, modifying details regarding one or more steps and/or screws, removing one or more steps and/or screws, or any combination of the foregoing).

In some embodiments, the predetermined action may be or include displaying the torque data or some portion thereof, and/or the results of the evaluation or some portion thereof, via a user interface such as the user interface 112 or 212.

The present disclosure encompasses embodiments of the method 300 that comprise more or fewer steps than those described above. Additionally, although described primarily in connection with one or more drilling, tapping, and/or screw insertion procedures, the method 300 may be used in connection with any procedure in which one or more torque characteristics may be measured and evaluated to yield actionable information.

Figure 3B:
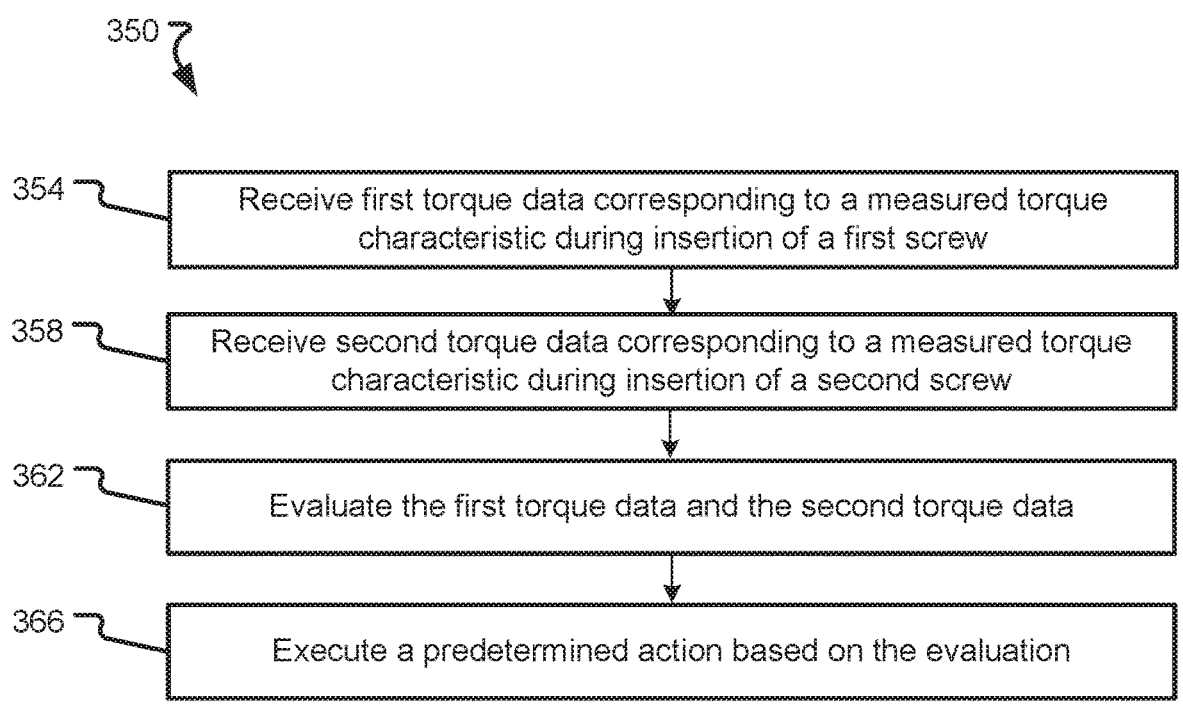
FIG. 3B is another flowchart of a method according to at least one embodiment of the present disclosure.

Turning now to FIG. 3B, a method 350 of using torque data during a surgical procedure comprises receiving first torque data corresponding to a measured torque characteristic during insertion of a first screw (step 354). The receiving step 354 may be the same as or similar to the receiving step 304 of the method 300. For example, the first torque data may be raw data output by a torque sensor 136 or 236, or the first torque data may be processed data generated based on raw data output by the torque sensor 136 or 236. The measured torque characteristic may be or correspond to one or more of peak torque, accumulated torque, and/or RMS torque, although in some embodiments, the torque data may be or correspond to a different torque characteristic. The first torque data may be received directly from the torque sensor 136 or 236, or via one or more processors, communication interfaces, or other components described herein. For example, the first torque data may be transmitted from a communication interface 138 to a cloud 148, and from the cloud 148 to the communication interface 112 before arriving at the processor 104. As another example, where the power tool 200 is being used, the first torque data may simply be transmitted across an internal bus from the torque sensor 236 to the processor 204, whether directly or via the communication interface 208 and/or the memory 216.

The first screw may be, for example, any screw that is being inserted into a patient, for example as part of or otherwise in connection with a surgical plan. The screw may be a screw intended to hold a fixation rod or other apparatus or implant useful for correcting, treating, or otherwise addressing a spinal condition or other patient condition. The first screw may be, for example, a pedicle screw.

The method 350 also comprises receiving second torque data corresponding to a measured torque characteristic during insertion of a second screw (step 358). The first torque data may be received at a first time, and the second torque data may be received at a second time after the first time. The second torque data may be or correspond to the same measured torque characteristic(s) as the first torque data. Alternatively, the second torque data may be or correspond to one or more measured torque characteristics different than the measured torque characteristic(s) of the first torque data.

The second torque data may be received in the same manner as the first torque data. For example, the second torque data may be raw data output by a torque sensor 136 or 236, or the second torque data may be processed data generated based on raw data output by the torque sensor 136 or 236. The measured torque characteristic may be or correspond to one or more of peak torque, accumulated torque, RMS torque, or another torque characteristic. The second torque data may be received directly from the torque sensor 136 or 236, or via one or more processors, communication interfaces, or other components described herein. For example, the second torque data may be transmitted from a communication interface 138 to a cloud 148, and from the cloud 148 to the communication interface 112 before arriving at the processor 104. As another example, where the power tool 200 is being used, the second torque data may simply be transmitted across an internal bus from the torque sensor 236 to the processor 204, whether directly or via the communication interface 208 and/or the memory 216.

Like the first screw, the second screw may be, for example, any screw that is being inserted into a patient, for example as part of or otherwise in connection with a surgical plan. The screw may be a screw intended to hold a fixation rod or other apparatus or implant useful for correcting, treating, or otherwise addressing a spinal condition or other patient condition. The second screw may be, for example, a pedicle screw.

The method 350 also comprises evaluating the first torque data and the second torque data (step 362). The evaluation may be the same as or similar to the evaluating described above in connection with the step 308. The evaluating may, for example, involve comparing one or both of the first torque data and the second torque data (or some portion thereof) to a predetermined threshold, or applying one or more predetermined criteria to the first torque data and the second torque data (or some portion thereof). The evaluating may comprise comparing one or more aspects of the first torque data against one or more aspects of the second torque data. The evaluating may comprise determining whether to revise a surgical plan in light of the first torque data and the second torque data (or some portion or aspect thereof). For example, if the first torque data and the second torque data indicate that an appropriate amount of torque was necessary and/or used to insert the first screw and the second screw, then a determination may be made that the surgical plan should remain unchanged, or that the surgical plan should be revised to omit a screw that had previously been planned for insertion (e.g., because the first and second torque data support a conclusion that the first and second screws are properly seated and will be sufficient without insertion of the screw in question). Alternatively, if the first torque data and the second torque data indicate that less than an appropriate amount of torque was necessary and used to insert the first screw and the second screw, then the evaluation may result in a conclusion that the surgical plan should be revised to add one or more additional screws for insertion (e.g., because the first and second torque data support a conclusion that the first and second screws are loosely seated and will not be sufficient without the insertion of additional screws).

The method 350 also comprises executing a predetermined action based on the evaluation (step 366). The executing may be the same as or similar to the executing described above in connection with the step 312. Similarly, the predetermined action may be the same as or similar to any predetermined action described above. The predetermined action may comprise removing a fully or partially inserted screw from an anatomical feature of a patient before inserting a different screw, re-drilling a previously drilled hole, re-tapping a previously tapped hole, or making another change. In some embodiments, the predetermined action may be or comprise revising the surgical plan (e.g., where the evaluation concludes that one or more screws should be added to or omitted from the surgical plan, the surgical plan may be revised accordingly). The predetermined action may also be or comprise leaving the surgical plan unchanged (e.g., where the evaluation concludes that no change to the surgical plan is necessary). In some embodiments, the predetermined action may be or comprise generating and/or displaying a recommendation to the user corresponding to any predetermined action described above.

Although the method 350 is described as including steps for receiving first torque data corresponding to a measured torque characteristic during insertion of a first screw and receiving second torque data corresponding to a measured torque characteristic during insertion of a second screw, embodiments of the present disclosure including methods such as the method 350 in which additional torque data is received, corresponding to a measured torque characteristic during insertion of one or more additional screws. Thus, in some embodiments, torque data corresponding to a measured torque characteristic during three, four, five, six, seven, eight, nine, ten, or more screws may be received and evaluated.

The present disclosure encompasses embodiments of the method 350 that comprise more or fewer steps than those described above. Additionally, although described in connection with two or more screw insertion procedures, the method 350 may be used in connection with any procedure in which one or more torque characteristics may be measured and evaluated during two or more aspects of a given surgical procedure (e.g., two drilling procedures, or two tapping procedures, or a drilling procedure and a tapping procedure, or a drilling procedure and a screw insertion procedure, or any other combination of two or more aspects of the surgical procedure).

Figure 4:
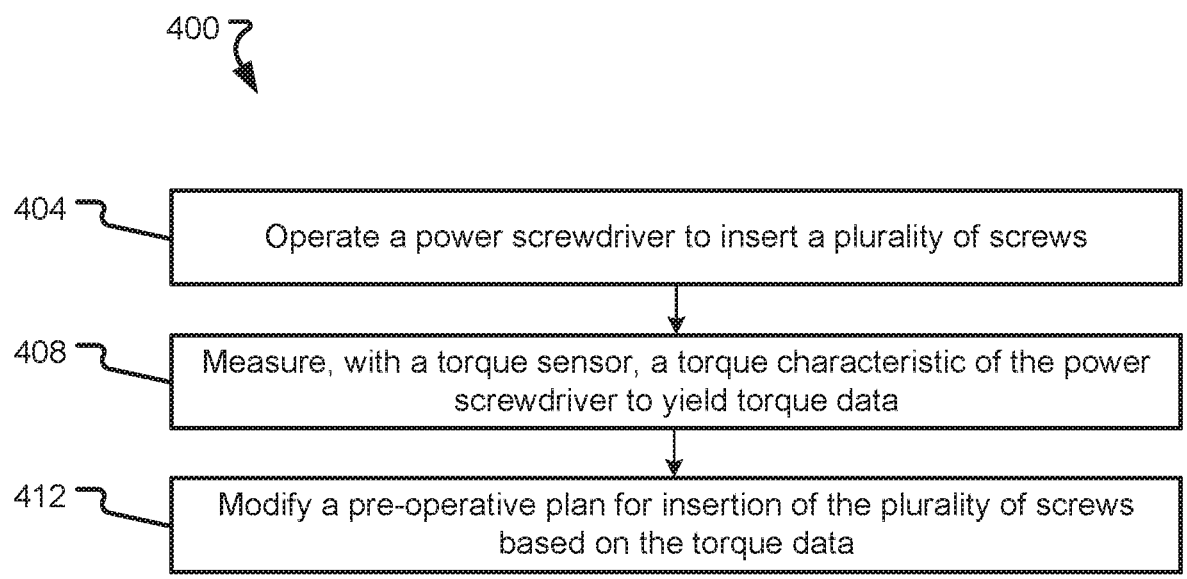
FIG. 4 is another flowchart of a method according to at least one embodiment of the present disclosure.

Turning now to FIG. 4, a method 400 of utilizing torque data in connection with a surgical procedure comprises operating a power screwdriver to insert a plurality of screws (step 404). The power screwdriver may comprise or otherwise be connected to a torque sensor that measures torque generated and/or applied by the power screwdriver. The power screwdriver may be, for example, a power tool 132 or a power tool 200 as described above. The power screwdriver may be a handheld device operated based on user input (e.g., by a user squeezing a trigger that causes the power screwdriver to activate), and/or the power tool may be configured to be held and/or operated by a robotic arm. The power screwdriver may be specifically adapted for use during surgeries.

The screws inserted by the power screwdriver may be any surgical screws. In some embodiments, each of the plurality of screws is a pedicle screw, and each of the plurality of screws is inserted into a vertebra of a patient's spine. One or more of the plurality of screws may additionally or alternatively be other bone screws for insertion into other bones of the patient's anatomy.

The method 400 also comprises measuring, with a torque sensor, a torque characteristic of the power screwdriver to yield torque data. The measured torque characteristic may be or correspond to one or more of peak torque, accumulated torque, RMS torque, and/or any other torque characteristic. As noted above, the torque sensor may be built into or otherwise installed in or on the power screwdriver, or the torque sensor may be operably attached to the power screwdriver (e.g., attached in a way that allows the torque sensor to measure a torque generated and/or applied by the power screwdriver). The torque sensor may be the same as or similar to the torque sensor 136 and/or the torque sensor 236 described above. The torque data may be raw data output by the torque sensor, or the torque data may be processed data generated based on raw data output by the torque sensor.

The method 400 also comprises modifying a pre-operative plan for insertion of the plurality of screws based on the torque data. The pre-operative plan may be any surgical plan for a surgical procedure that involves the insertion of a plurality of screws. The pre-operative plan may identify one or more additional screws, beyond the plurality of screws, for insertion. The pre-operative plan may identify a specific screw type and/or size, or any other identifying information, for each screw identified in the plan. The pre-operative plan may identify, describe, and/or otherwise define one or more procedures in addition to screw insertion, such as drilling and/or tapping. In some embodiments, the pre-operative plan may identify, for example, a specific drill bit to use in a drilling procedure, a specific depth to which to drill in the drilling procedure, and/or a specific tap and/or die size and/or gauge to use in a tapping procedure. The pre-operative plan may define a specific position and orientation for insertion of each of one or multiple screws.

The modifying of the pre-operative plan may comprise changing any one or more details of the pre-operative plan based on the torque data. For example, the modifying may comprise removing from the pre-operative plan a screw that was identified for insertion in the original plan; adding to the original plan an additional screw for insertion that was not previously identified in the original plan; changing a type, size, or any other characteristic of a screw identified in the plan; changing a position and/or orientation of a screw identified for insertion in the plan; and/or adjusting any other aspect of the pre-operative plan in light of the torque data.

By way of example, if the torque data indicates that one or more of accumulated, peak, and/or RMS torque is below a predetermined threshold, then the pre-operative plan may be modified to call for a larger screw (e.g., a screw that will require more torque to insert) or to otherwise adjust the size of the screw, or to skip the screw, or to add an additional screw, or the re-drill or re-tap the hole in which the screw is to be inserted. An algorithm (such as an algorithm 128) may be used to select a larger or otherwise differently sized screw (whether from among a predetermined selection of screw sizes or not), or to determine whether to skip the screw altogether, or to determine whether (and if so, to what specifications) to re-drill or re-tap the hole associated with the screw.

As an alternative example, if the torque data indicates that one or more of accumulated, peak, and/or RMS torque is above a predetermined threshold, then the pre-operative plan may be modified to call for a smaller screw (e.g., a screw that will require less torque to insert), or to otherwise adjust the size of the screw, or to skip the screw, or to re-drill or re-tap the hole in which the screw is to be inserted. Here again, an algorithm (such as an algorithm 128) may be used to select a larger or otherwise differently sized screw (whether from among a predetermined selection of screw sizes or not), or to determine whether to skip the screw altogether, or to determine whether (and if so, to what specifications) to re-drill or re-tap the hole associated with the screw.

In some instances, the torque data may indicate or support a conclusion that no change to the screw, the screw position and/or orientation, the drilling and/or tap size, or any other aspect of the screw insertion procedure needs to be changed. Also in some instances, the torque data may be higher or lower than a corresponding predetermined threshold, but the screw may ultimately be inserted anyway as originally called for in the pre-operative plan. In any of the foregoing instances, the plan still may be updated to record the torque data and/or a summary thereof—whether for archival purposes, so that the plan may be used as machine learning training data, or for any other purpose.

The present disclosure encompasses embodiments of the method 400 that comprise more or fewer steps than those described above. Additionally, although described in connection with a power screwdriver and a plurality of screws, the method 400 may be used in connection with any procedure in which one or more torque characteristics of any power tool may be measured and evaluated during two or more aspects of a given surgical procedure (e.g., two drilling procedures, or two tapping procedures, or a drilling procedure and a tapping procedure, or a drilling procedure and a screw insertion procedure, or any other combination of two or more aspects of the surgical procedure).

Figure 5:
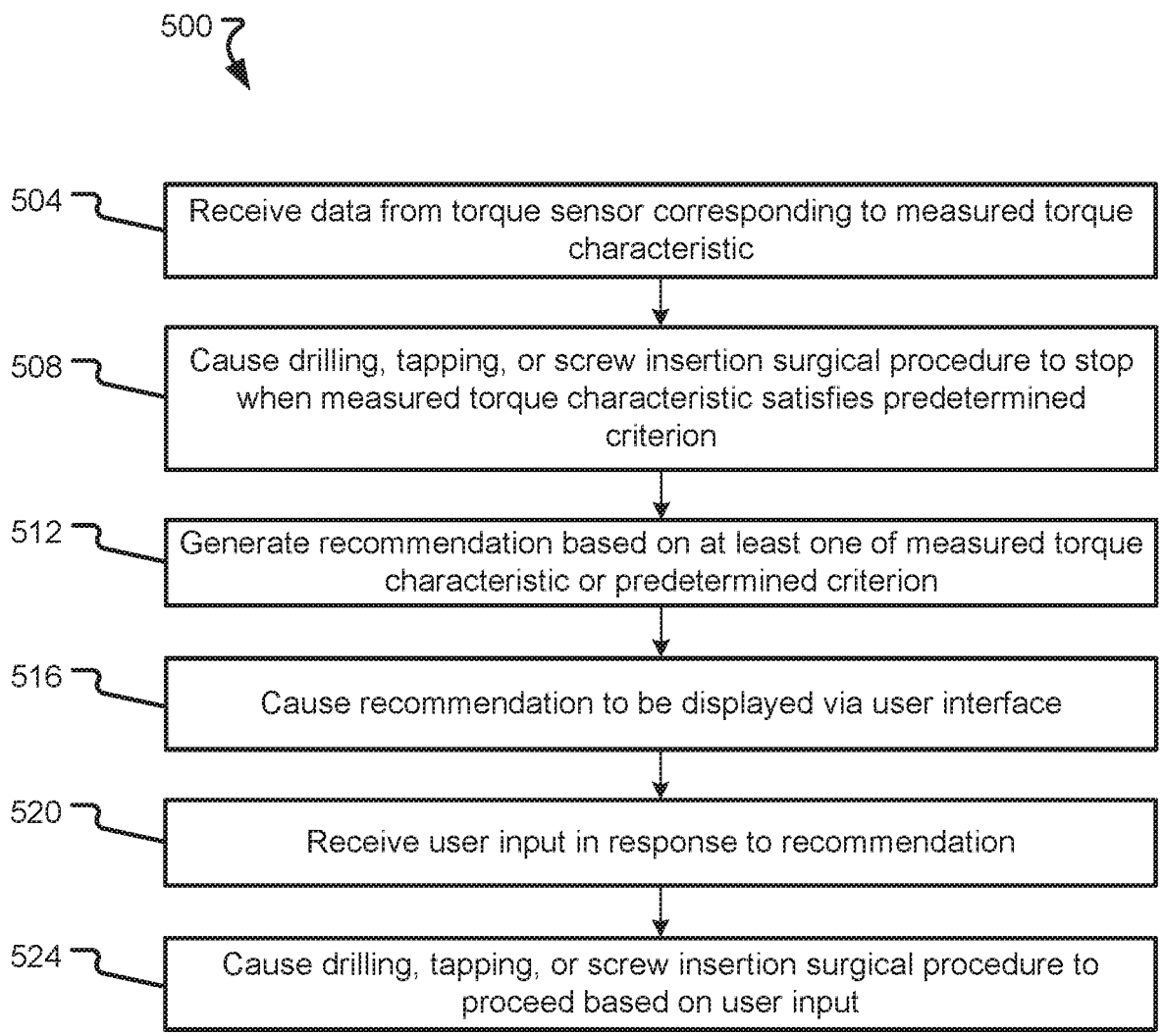
FIG. 5 is another flowchart of a method according to at least one embodiment of the present disclosure.

With reference now to FIG. 5, a method 500 for generating recommendations based on torque data comprises receiving data, from a torque sensor, corresponding to a measured torque characteristic (step 504). The torque sensor may be the same as or similar to the torque sensor 136 or 236, and may be configured to measure a torque characteristic of a power tool such as the power tool 132 and/or the power tool 200. The torque data may be raw data output by a torque sensor 136 or 236, or the torque data may be processed data generated based on raw data output by the torque sensor 136 or 236. The measured torque characteristic may be or correspond to one or more of peak torque, accumulated torque, RMS torque, and/or any other torque characteristic. The torque data may be received directly from the torque sensor, or via one or more processors, communication interfaces, or other components described herein. For example, the torque data may be transmitted from a communication interface such as the communication interface 138 to a cloud such as the cloud 148, and from the cloud to another communication interface such as the communication interface 112 before arriving at a processor such as the processor 104. On the other hand, where a power tool such as the power tool 200 is being used, the torque data may simply be transmitted across an internal bus from a torque sensor such as the torque sensor 236 to a processor such as the processor 204, whether directly or via a communication interface such as the communication interface 208 and/or a memory such as the memory 116.

The method 500 also comprises causing a drilling, tapping, or screw insertion surgical procedure to stop when the measured torque characteristic satisfies a predetermined criterion (step 508). The causing may occur by cutting a power supply to a motor or other device of the power tool, or by sending a control signal to a motor or other device of the power tool (or to a processor or other controller controlling a motor of the power tool), or in any other suitable manner. The causing may or may not be accompanied by a warning to the operator that the drilling, tapping, or screw insertion surgical procedure is going to be or is being stopped. The causing may occur substantially instantaneously, or via a gradual decrease in power, torque, RPM, or any other operating characteristic of the power tool.

The predetermined criterion may be or comprise that the measured torque characteristic has reached or exceed a predetermined threshold, or any other predetermined criterion described herein. The predetermined criterion may relate to only one torque characteristic (e.g., peak torque, accumulated torque, or RMS torque), or the predetermined criterion may relate to a combination of two or more torque characteristics. The predetermined criterion may comprise use of an algorithm, such as an algorithm 124, into which a measured torque characteristic is input, or against an output of which a measured torque characteristic is compared. The measured torque characteristic may be received and evaluated against the predetermined criterion on demand (e.g., in response to a user request or other input), periodically (e.g., every ten seconds, or every five seconds, or every second, or every half second, or every quarter second, or every tenth of a second), or continuously (e.g., in real time or near real time).

In some embodiments, the predetermined criterion may be based on historical data such as the historical data 120. For example, where historical data regarding one or more measured torque characteristics during a plurality of surgical procedures (e.g., drilling, tapping, screw insertion, or other surgical procedures) is available, and particularly where such historical data comprises information about patient outcomes, then the historical data may be used to generate one or more predetermined criteria useful for evaluating, for example, a likely outcome of the current procedure based on available torque data; whether a likely outcome of the current procedure may be improved by adjusting one or more aspects of a surgical plan for the current procedure; and/or whether a likely outcome of the surgical procedure may be improved by modifying one or more aspects of the procedure (e.g., in a manner that will affect one or more measured torque characteristics of the procedure going forward). Thus, for example, if the historical data suggests that outcomes are poor when peak torque reaches or surpasses a specific threshold during insertion of a screw, the predetermined criterion may comprise evaluating whether peak torque is approaching the specific threshold in question, and if so, removing the screw being inserted and inserting instead a smaller screw or a screw that otherwise requires less torque to insert.

The method 500 also comprises generating a recommendation based on at least one of the measured torque characteristic or the predetermined criterion (step 512). The recommendation may be the same as or similar to any other recommendation described herein, including with respect to the steps 312 and/or 366. In some embodiments, the recommendation is based on both the measured torque characteristic and the predetermined criterion. The recommendation may be, comprise, or relate to changing one or more parameters of the procedure in question (e.g., of a drilling procedure, a tapping procedure, and/or a screw insertion procedure), whether by modifying a pre-operative or other surgical plan, or otherwise; or to changing one or more settings of a power tool being used in connection with the procedure (e.g., a power tool 132 or 200).

The method 500 also comprises causing the recommendation to be displayed via a user interface (step 516). The recommendation may be displayed with text and/or with one or more graphics. In some embodiments, the recommendation may additionally or alternatively be conveyed audibly (e.g., using a pre-recorded or computer-generated voice, or one or more audible signals) or in another non-visual manner. The user interface may be the same as or similar to a user interface 112 or 212.

The method 500 also comprises receiving a user input in response to the recommendation (step 520). The user input may be received, for example, via a user interface such as the user interface 112 or 212. The input may be or comprise a selection of one of a plurality of options (e.g., displayed in conjunction with the recommendation or otherwise). The input may be or comprise one or more modifications to an electronic surgical plan.

The method 500 also comprises causing the drilling, tapping, or screw insertion surgical procedure to proceed based on user input (step 524). Thus, for example, where the user input indicates that a larger screw should be used, the causing may comprise causing a partially inserted screw to be removed and set aside or otherwise discarded, a new screw of the desired size to be selected, and the new screw to be inserted. As another example, where the user input indicates that no change is needed, the surgical procedure may proceed as originally planned. As yet another example, where the user input indicates that a hole into which a screw is being inserted needs to be re-drilled and/or re-tapped, the causing may comprise causing a partially inserted screw to be removed and set aside or otherwise discarded, an appropriately sized drill bit or tap to be operatively connected to the power tool, and the hole in question to be re-drilled and/or re-tapped, respectively.

The present disclosure encompasses embodiments of the method 500 with more or fewer steps than those described above.

As may be appreciated based on the foregoing disclosure, the present disclosure encompasses methods with fewer than all of the steps identified in FIGS. 3A, 3B, 4, and 5 (and the corresponding description of the methods 300, 350, 400, and 500), as well as methods that include additional steps beyond those identified in FIGS. 3A, 3B, 4, and 5 (and the corresponding description of the methods 300, 350, 400, and 500).

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:
1. A surgical system comprising:
a power tool that generates torque;
a torque sensor for measuring a torque characteristic of the power tool;
a user interface;
at least one processor; and
a memory storing instructions for execution by the at least one processor that, when executed, cause the at least one processor to:

receive torque data from the torque sensor, the torque data corresponding to the measured torque characteristic;

evaluate the torque data; and execute a predetermined action based on the evaluation, wherein the predetermined action comprises at least one of: (i) automatically adjusting a surgical plan to change a number of screws used in the surgical plan and (ii) providing a recommendation for approval by a surgeon that includes adjusting the surgical plan to change the number of screws used in the surgical plan.

2. The surgical system of claim 1, wherein the measured torque characteristic is a peak torque, and the evaluation comprises comparing the peak torque to a predetermined threshold.

3. The surgical system of claim 2, wherein when the peak torque exceeds the predetermined threshold, the predetermined action comprises stopping the power tool.

4. The surgical system of claim 1, wherein the measured torque characteristic is an accumulated torque, and the evaluation comprises comparing the accumulated torque to a predetermined threshold.

5. The surgical system of claim 4, wherein when the accumulated torque is less than the predetermined threshold, the predetermined action comprises causing a recommendation to be displayed via a user interface.

6. The surgical system of claim 5, wherein the power tool is a screwdriver, and the recommendation comprises a recommendation to select a larger screw.

7. The surgical system of claim 1, wherein the power tool is a screwdriver, the torque data corresponds to the measured torque characteristic during insertion with the screwdriver of a first screw, and the memory stores additional instructions for execution by the at least one processor that, when executed, further cause the at least one processor to:

receive second torque data from the torque sensor, the second torque data corresponding to the measured torque characteristic during insertion with the screwdriver of a second screw.

8. The surgical system of claim 7, wherein the evaluating comprises evaluating the torque data and the second torque data.

9. The surgical system of claim 1, wherein the predetermined action comprises stopping the power tool and requesting user input.

10. The surgical system of claim 1, wherein the surgical plan is adjusted to increase the number of screws used in the surgical plan based on the evaluation.

11. The surgical system of claim 1, wherein the surgical plan is adjusted to decrease the number of screws used in the surgical plan based on the evaluation.

12. A system, comprising:

a torque sensor for measuring a torque characteristic of a power tool;

a user interface;

at least one processor; and a memory storing instructions for execution by the at least one processor that, when executed, cause the at least one processor to:

receive torque data from the torque sensor, the torque data corresponding to the measured torque characteristic;

evaluate the torque data;

automatically generate a recommendation for display by the user interface based on the evaluation of the torque data, wherein the recommendation comprises a description of a surgical plan adjustment; and cause the user interface to display the description of the surgical plan adjustment.

13. The system of claim 12, wherein the description of the surgical plan adjustment provides an instruction to change a number of screws used in the surgical plan.

14. The system of claim 12, wherein the description of the surgical plan adjustment provides an instruction to utilize a different screw than was previously used as part of the surgical plan.

15. The system of claim 12, wherein the description of the surgical plan adjustment provides an instruction to re-drill a previously drilled hole.

16. The system of claim 12, wherein the description of the surgical plan adjustment provides an instruction to re-tap a previously tapped hole.

17. The system of claim 12, wherein the description of the surgical plan adjustment provides an instruction to remove at least a part of an anatomical feature.

18. The system of claim 12, wherein the torque data comprises first torque data and second torque data indicating whether or not a first screw and second screw were seated according to the surgical plan.

19. A system, comprising:

at least one processor; and a memory storing instructions for execution by the at least one processor that, when executed, cause the at least one processor to:

receive torque data from a torque sensor, the torque data corresponding to a measured torque characteristic of a power tool;

evaluate the torque data;

automatically generate a recommendation based on the evaluation of the torque data, wherein the recommendation comprises a description of a surgical plan adjustment; and cause a user interface to display the description of the surgical plan adjustment.

20. The system of claim 19, wherein the description of the surgical plan adjustment provides an instruction to change a number of screws used in the surgical plan.

* * * * *